United States Patent [19]

Baillie

[11] Patent Number: 4,759,637

[45] Date of Patent: Jul. 26, 1988

[54] APPARATUS AND METHOD FOR DETERMINING WATER DEW POINT

[75] Inventor: Lloyd A. Baillie, Plano, Tex.

[73] Assignee: Atlantic Richfield Company, Los Angeles, Calif.

[21] Appl. No.: 905,019

[22] Filed: Sep. 8, 1986

[51] Int. Cl.[4] ............................................. G01N 25/02
[52] U.S. Cl. ......................................... 374/28; 374/27
[58] Field of Search ................................... 374/16–20, 374/27, 28; 73/29, 335, 336.5, 863.11, 863.12, 863.61, 863.71; 250/573–576, 564–565

[56] References Cited

U.S. PATENT DOCUMENTS

| 2,562,181 | 7/1951 | Frommer | 250/574 |
| 3,134,259 | 5/1964 | Hallmarken | 374/28 |
| 3,216,257 | 11/1965 | Ford | 73/335 |
| 4,115,229 | 9/1978 | Capone | 73/863.61 |

FOREIGN PATENT DOCUMENTS

| 170820 | 5/1952 | Fed. Rep. of Germany | 374/20 |
| 2103089 | 7/1972 | Fed. Rep. of Germany | 73/29 |
| 317306 | 8/1929 | United Kingdom | 374/20 |
| 894520 | 12/1981 | U.S.S.R. | 73/29 |

Primary Examiner—William A. Cuchlinski, Jr.
Assistant Examiner—W. Morris Worth
Attorney, Agent, or Firm—Frank J. Uxa; Michael E. Martin

[57] ABSTRACT

An apparatus useful for determining the water dew point temperature of a water, hydrocarbon-containing gaseous material in which the water dew point is lower than the hydrocarbon dew point temperature comprises: an elongated column capable of being filled with liquid in substantial equilibrium with the water, hydrocarbon-containing gaseous material and placed in an environment having a temperature reduced relative to the water dew point of the material; a signal source acting to send signals through the column; a signal receiver acting to receive the signals sent through the column; a control system acting in response to the received signals to control the temperature of the liquid in the column at substantially the water dew point of the water, hydrocarbon-containing gaseous material; and a temperature indicator acting to determine the temperature of the liquid in the column. Improved methods for determining such water dew point temperature are also disclosed.

16 Claims, 1 Drawing Sheet

APPARATUS AND METHOD FOR DETERMINING WATER DEW POINT

This invention relates to a system for determining the water dew point temperature of a water, hydrocarbon-containing gaseous material. More particularly the invention relates to an apparatus and method for determining the water dew point temperature of a water, hydrocarbon-containing gaseous material in which the water dew point temperature is low relative to the hydrocarbon dew point temperature.

Often, relatively small amounts of water-vapor become combined with and/or naturally occur in hydrocarbon gaseous or vaporous materials. This water-vapor can be troublesome in producing, transporting, processing and using these hydrocarbon materials. Therefore, hydrocarbon gaseous materials often are subjected to drying and other operations to reduce water content. Because of the small initial concentrations of water-vapor, it may be difficult to monitor either the initial water-vapor concentration or the reduced water-vapor concentration of such hydrocarbon gaseous materials.

One approach to monitoring the water-vapor concentration in hydrocarbons gases is to monitor the water dew point temperature of the hydrocarbon gaseous material. The water dew point temperature of a gaseous material is defined as that temperature at which water vapor begins to condense into liquid phase water. Knowing the water dew point temperature, one can easily calculate the water concentration in the gaseous material. In certain instances, the hydrocarbon gaseous material is required to meet a water dew point temperature specification. For example, in transporting natural gas, the pipeline often has a maximum specification on water dew point temperature which is not to be exceeded. Thus, the individual gas producers, as well as the pipeline operator, need a rapid, reliable and easy to operate system to determine, preferably on an on-line or substantially continuous basis, the water dew point temperature of the natural gas entering and/or being transported in the pipeline. Such determinations are made more difficult since in many situations, the hydrocarbon dew point temperature is higher than the water dew point temperature. In other words, in these instances the condensation of the hydrocarbon tends to obscure the condensation of the water, making it difficult to determine at what temperature the water in the material begins to condense. Clearly, it would be advantageous to provide an improved water dew point determination system for these situations.

Therefore, one object of the present invention is to provide an improved apparatus useful for determining the water dew point temperature of a water, hydrocarbon-containing gaseous material having a relatively low water dew point.

Another object of the present invention is to provide an improved method for determining the water dew point temperature of a water, hydrocarbon-containing gaseous material having a relatively low water dew point. Other objects and advantages of the present invention will become apparent hereinafter.

An improved apparatus and method useful for determining the water dew point temperature of a water, hydrocarbon-containing gaseous material in which the water dew point temperature is low relative to the hydrocarbon dew point temperature have been discovered. In one broad aspect, the present apparatus comprises:

column means capable of being filled with a liquid in substantial equilibrium with the water, hydrocarbon-containing gaseous material and placed in an environment having a lower temperature relative to the water dew point temperature of the gaseous material;

signal source means acting to send signals through at least a portion of the liquid in the column means;

signal receiver means acting to receive signals from the signal source means after the signals have passed through at least a portion of the liquid in the column means;

control means acting in response to the received signals to control the temperature of the liquid in the column means at substantially the water dew point temperature of the gaseous material; and temperature indicator means acting to determine the temperature of the liquid in the column means.

In another broad aspect, the present invention is directed to a method for determining the water dew point temperature of such water, hydrocarbon-containing materials which comprises:

(a) placing a liquid in substantial equilibrium with the gaseous material in an environment having a temperature less than the water dew point temperature of the gaseous material;

(b) passing signals through at least a portion of the liquid;

(c) receiving the signals after the signals have passed through the liquid;

(d) controlling the temperature of the liquid at substantially the water dew point temperature in response to the received signals; and (e) measuring the temperature of the liquid.

The present apparatus and method provide for rapid and reliable water dew point temperatures determinations which have heretofore been obtained only through difficult, tedious and lengthy procedures. The present system is particularly suited for use in situations where substantially continuous, on-line monitoring of the water dew point temperature is required or desired. For example, the present system may be used to substantially continuously monitor the water dew point of natural gas streams being transported by pipelines. The present system takes advantage of the property of water, hydrocarbon-containing gaseous or vaporous materials wherein turbidity results when water and hydrocarbon condense together. The received signals are altered as the result of this condensation turbidity and the present system responds to these altered signals by controlling the temperature of the liquid at the water dew point, which can be easily measured, e.g., by a thermometer or thermocouple assembly. The present "control" approach to water dew point temperature determination not only provides rapid and reliable results, but also makes these determinations largely automatically, i.e., without human intervention, using a unique combination of components.

The phrase "a liquid in substantial equilibrium with the gaseous material" as used herein refers to a liquid having a composition substantially the same as the composition of a liquid derived by subjecting the gaseous material to the conditions of pressure and temperature existing in the present column means or in the liquid employed in the present method.

The present apparatus preferably further comprises first and second leg means each of which has a first end near the mutually opposing first end and second ends, respectively, of the column means. These first and second leg means are in fluid communication with the column means. A third leg means is preferably included and is situated so that the second end of each of the first and second leg means terminates in the third leg means to provide fluid communication between the first, second and third leg means. Preferably, the first and second leg means, and the column and third leg means are substantially parallel. The first and second leg means are preferably perpendicular to the column and third leg means. The functioning of the first, second and third leg means is as detailed herein. However, preferably at least a portion of the water, hydrocarbon-containing gaseous material condensed into a liquid flows through the first, second and third leg means before passing into the column means. This somewhat circuitous route to the column means provides time and space to condition or acclimate or substantial equilibrate the gaseous material to the temperature and pressure conditions existing in the column means. For example, it is preferred that the first, second and third leg means and the column means be wrapped with a heating means, e.g., conventional electrical heating tape, from the control means. This heating means provides energy to the column means and to each of the leg means, as desired, to control the temperature of the material therein.

The second leg means preferably includes an inlet means, e.g., located near the end of the second leg means which terminates in the column means. This inlet means acts as a conduit to allow water, hydrocarbon-containing material to be introduced into the apparatus. The third leg means preferably includes an outlet means to allow material to exit from the apparatus. Preferably, both the inlet means and outlet means function simultaneously and there is a circulation of material in the apparatus so that substantially continuous on-line determinations of water dew point temperature can be provided.

The outlet means may be structured in any suitable fashion. Since the water, hydrocarbon-containing gaseous material, such as natural gas under substantial pressure, is partially condensed in the present apparatus, the outlet means is preferably structured to include a weir means, an outlet conduit and a pressure regulator means. The weir means is situated so that substantially all of the material entering the first leg of the system is liquid. The outlet conduit, preferably located downstream from the weir means, is preferably maintained at conditions, e.g., of temperature and pressure, so that substantially all of the material existing in the apparatus is gaseous or vaporous. The pressure regulator means, e.g., a conventional pressure regulator and related equipment, is preferably situated in association with the outlet conduit and acts to maintain a predetermined pressure in the apparatus. A separate heating means is preferably associated with the outlet conduit to provide energy to the material leaving the apparatus so that such material is substantially gaseous or vaporous.

The signal source means and signal receiver means may be any suitable combination of components. These two means should be compatible in that the signal emitted or sent by the source means should be suitable for being received by the receiver means. Also, the signals sent by the source means should be alterable by the presence and degree of turbidity of the liquid in the column means. Although any suitable signals may be employed, it is preferred that the signals be light signals, more preferably visible light signals. If light signals are used, the preferred signals receiver means includes a photoresistor, such as a conventional cadmium sulfide photoresistor.

As noted above, the control means preferably includes heating means to provide energy to the column and leg means. The control means also preferably includes relay circuit means which acts in response to the received signals, i.e., signals received by the signal receiver means, to energize the heating means. Such relay signal means may include a conventional temperature relay switch, such as produced by Gardsman, which is regulated, i.e., turned on and off, in response to the received signals, e.g., in response to the intensity of the light signals received by a photoresistor which is part of an electrical control circuit.

The temperature indicator means may include any temperature sensor useful to determine the temperature of the liquid in the column means. One particularly useful embodiment includes a thermocouple, e.g., a conventional bi-metallic thermocouple, situated in proximity to the first leg means and communicating with a temperature read-out device, e.g., a conventional electrical temperature indicator. Because of the preferred configuration of the present apparatus, the temperature of the material in the first leg means is substantially the same as the temperature in the column means. It is preferred to not have the thermocouple in the column means so that the signals may pass through the liquid in the column means without undue extraneous interference. In order to provide a permanent record of the water dew point temperatures determined by the present apparatus, it is preferred that the temperature indicator means further include recording means, e.g., printer, chart recorder or other display device, capable of providing a record of the determined water dew point temperatures.

In the present method, it is preferred that the signals being sent are substantially constant. Preferably the signals are passed into the column means at or near the first end of the column means and are received at or near the opposing second end of the column means. The signals being passed through the column means are preferably light signals and the temperature of the material is controlled in response to the intensity of the received light signals.

The preferred general direction of flow of the material passes sequentially through the second leg means, the third leg means, the first leg means and the column means, provided that the material in the first leg and column means is substantially liquid. At least a portion of the liquid in the column means is preferably recirculated to the second leg means.

The solubility of water in liquid hydrocarbons is very low and is extremely low in the case of low molecular weight hydrocarbons, such as those condensed from gas flow streams. Consequently, any water detected with the liquid phase in the apparatus will be liquid water present as droplets. The presence of these droplets indicates that the gas phase is at or below its water dew point, and the turbidity associated with the presence of water droplets makes the water dew point detectable. If the gas phase water were in equilibrium with the trace of dissolved water in the liquid phase, then the water vapor pressure in the system would be equal to the mole fraction of water in the liquid (much less than 1.0) times the vapor pressure of the pure liquid water. Under these conditions, the vapor would be far from its water dew point; consequently, when vapor is at or below its water dew point then the vapor must be in equilibrium with pure liquid water, not dissolved water.

By "substantially hydrocarbon" is meant a gaseous material which includes hydrocarbon molecules and which becomes turbid as water condenses from a liquid which is in substantial equilibrium with the gaseous material, e.g., at the water dew point temperature of the gaseous material. The substantially hydrocarbon gaseous material may include other, non-hydrocarbon components, even in relatively large concentrations, provided that such material exhibits the water condensation/turbidity feature described above.

In general, and except as otherwise provided for herein, the apparatus of the present invention may be fabricated from any suitable material or combination of materials of construction. The material of construction used for each component of the present apparatus may be dependent upon the particular application involved. Of course, the apparatus should be made of materials which are substantially unaffected, except for normal wear and tear, by the conditions at which the apparatus is normally operated. In addition, such material or materials of construction should have no substantial detrimental effect on the water, hydrocarbon-containing gaseous material the water dew point temperature of which is being determined.

These and other aspects and advantages of the present invention are set forth in the following detailed description and claims, particularly when considered in conjunction with the accompanying drawings in which like parts bear like reference numerals. In the drawings:

Figure 2:
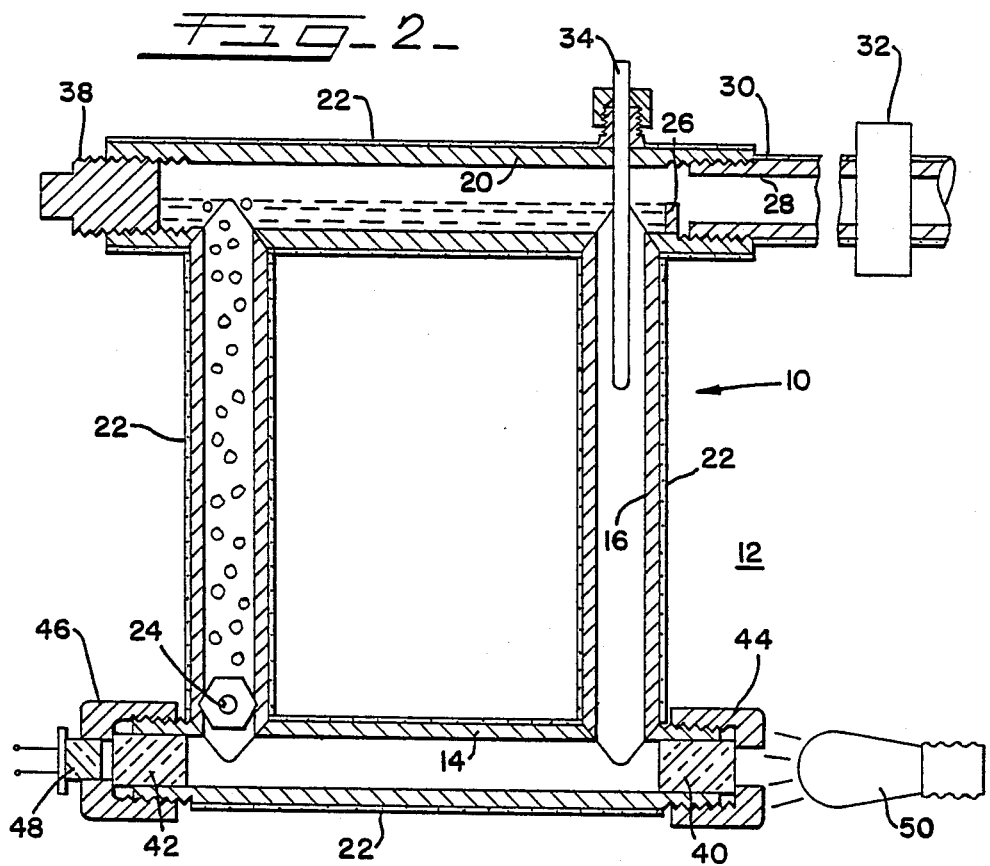
FIG. 2 is a front plan view, partly in cross-section showing certain components of an embodiment of the present apparatus which can be used in conjunction with the control means shown in FIG. 1.

Referring first to FIG. 2, a rectangular piping system, shown generally at 10, is placed in a refrigerated environment 12, e.g., in a thermostatted freezer compartment of about one (1) cubic foot in volume. System 10 includes a column means comprising a bottom column 14, a first leg 16, a second leg 18 and a top leg 20. Column 14 and legs 16, 18 and 20 are wrapped with an electric resistance heating tape 22. As can be seen from FIG. 2, both column 14 and top leg 20 are substantially horizontal and first leg 16 and second leg 18 are substantially vertical. There is fluid communication between column 14 and legs 16, 18 and 20. Each of column 14, and legs 16, 18 and 20 is constructed of conventionally sized, e.g., schedule 80, steel pipe.

Near the bottom of second leg 18 is an inlet port 24 through which water, hydrocarbon-containing material enters system 10. Top leg 20 includes a weir 26, and an outlet conduit 28 is threadedly secured to top leg 20. Outlet conduit 28 is wrapped with a separate electric resistance heating tape 30 which provides heat to outlet conduit 28 so that all material exiting system 10 by outlet conduit 28 is substantially vaporous. A pressure regulator 32 is provided to control or regulate the amount of pressure in system 10, as desired. Extending downwardly through top leg 20 into first leg 16 is a thermowell 34 which houses a thermocouple 36. A steel plug 38 is threaded into the end of third leg 20 opposite outlet conduit 28.

Glass plugs 40 and 42 are fitted into the ends of column 14 so as to be able to withstand substantial pressure. Pipe caps 44 and 46 are threadedly secured to opposing ends of column 14. A conventional cadmium sulfide photoresistor 48 is fitted into the central hole of pipe cap 46. A light bulb 50 is situated so that it emits a constant light signal through the central hole of pipe cap 44 and glass plug 40 into the space between glass plugs 40 and 42. Photoresistor 48 is situated to receive light signals from this space which pass through glass plug 42.

Figure 1:
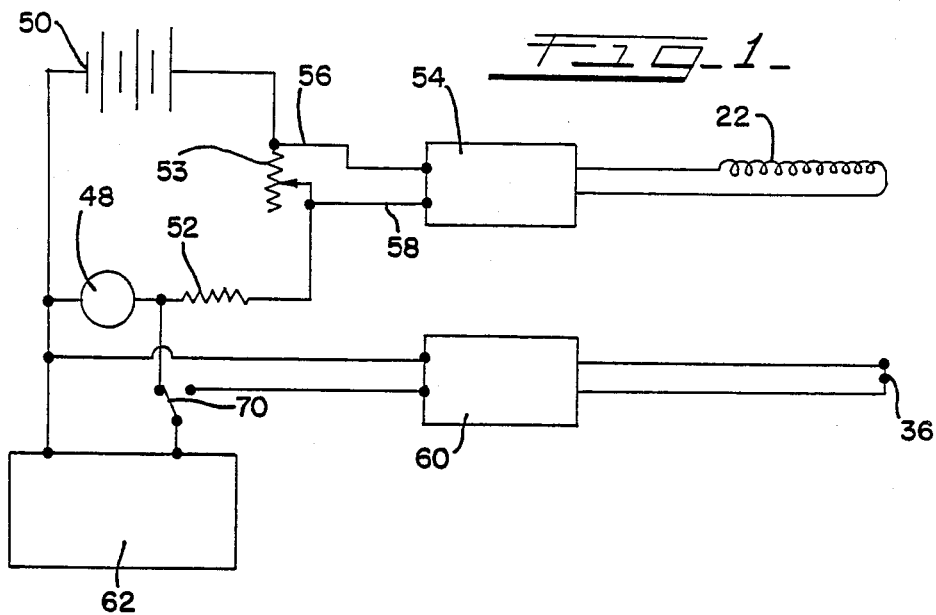
FIG. 1 is a schematic circuit diagram illustrating one embodiment of the control means of the present invention.

Referring now to FIG. 1, photoresistor 48 is connected in series with a storage battery 50, a fixed resistor 52 and a variable resistance heliopot 53. A conventional temperature relay, e.g., a Gardsman temperature relay, 54 is connected by wires 56 and 58 to sense the electric potential or voltage across heliopot 53. Based upon the voltage across heliopot 53, relay 54 will energize heating tape 22 to provide energy to the water, hydrocarbon-containing material in system 10.

Thermocouple 36 is connected to a temperature indicator 60, which provides a visual display of the temperature measured by thermocouple 36.

The electric potential across photoresistor 48 is measured by a millivolt recorder 62 which includes a chart recorder to provide a permanent record of the voltage across photoresistor 48.

Although system 10 and the circuitry associated with photoresistor 48 are not limited to any specific application, the functioning of these components can be illustrated by on-line determinations of the water dew point temperature of a natural gas stream flowing through a transportation pipeline operating at 650 psig. and about 88 degrees F. The natural gas contains a small amount of water and has a composition in volume percent of 76% methane, 12% carbon dioxide, 6% ethane, 3% propane and 3% heavier material. The hydrocarbon dew point temperature of this material is near 88 degrees F., but the desired water dew point temperature is near −25 degrees F. At −25 degrees F., roughly 10% of the material will condense.

A slip stream of natural gas from the pipeline is continuously introduced into system 10 through inlet port 24. Space 12 is maintained at a temperature of −40 degrees F. The vapors in second leg 18 produce a stream of bubbles, and cause liquid circulation, from column 14, by reducing the average density of that side of system 10. The bubbles disengage in top leg 20, which has a larger diameter than column 14 or first and second legs 16 and 18. Top leg 20 runs about one half full of liquid. From here, most of the liquid flows down first leg 16 past thermowell 34 where its temperature is sensed by thermocouple 36. Excess liquid, e.g., resulting from hydrocarbon condensation, flows over weir 26 into outlet conduit 28 where it is re-vaporized by heat from separate heating tape 30. All vapors then leave system 10 through pressure regulator 32, e.g., to be reinjected into the natural gas pipeline.

The liquid in first leg 16 circulates into column 14. If water droplets are present in the circulating liquid, the resulting turbidity scatters the light and attenuates the light beam, which causes the electrical resistance of photoresistor 48 to increase. The electrical resistance of photoresistor varies inversely with the light intensity reaching it.

The potential across photoresistor 48 is measured by millivolt recorder 62, so that the onset of turbidity caused by water condensation is visible on the chart recorder as an increase in voltage signal. Simultaneously, the voltage across fixed resistor 52 and heliopot 53 drops. For example, if storage battery 50 produces nine volts, fixed resistor 52 is 100,000 ohms, the resistance of heliopot 53 is 500 ohms and the resistance of photoresistor 48 increases from 100,000 ohms to 200,000 ohms, the voltage signal across photoresistor 48 will increase from 4.489 volts to 5.990 volts while the voltage signal across heliopot 53 will decline from 22.44 millivolts to 14.98 millivolts.

The millivolt signals sent to temperature relay 54 through wires 56 and 58 mimics the signal from a thermocouple when the temperature drops. Therefore, temperature relay 54 can be made to energize heating tape 22 wrapped around column 14 and legs 16, 18 and 20 in response to an increase in light attenuation, caused by turbidity from water condensation. The temperature of the liquid as sensed by thermocouple 36 is controlled at the temperature corresponding to the onset of turbidity, i.e., the water dew point temperature of the liquid in column 14.

Once temperature is controlled properly, a switch 70 can be thrown which allows millivolt recorder 62 to record the output of temperature indicator 60. This feature provides a continuous record of the water dew point temperature of the natural gas being introduced into system 10 in column 14.

Since the present apparatus and method allow for substantially continuous, on-line water dew point temperature determinations, the present invention is particularly useful in conjunction with controlling the operation of a transportation pipeline and the like on a real time basis. For example, any variance from the pipeline's or product's moisture specification is promptly identified so that corrective measures can be taken.

While this invention has been described with respect to various specific embodiments and examples, it is to be understood that the invention is not limited thereto and that it can be variously practiced within the scope of the following claims.

The embodiments of the present invention in which an exclusive right or privilege is claimed are as follows:

1. Apparatus for substantially continuously monitoring the water dew point temperature of a water, hydrocarbon-containing gaseous material flowing through a pipeline and wherein the water dew point temperature is lower than the hydrocarbon dew point temperature, said apparatus comprising:

column means having opposed first and second ends and being operable to be filled with liquid formed from condensed portions of said gaseous material and in substantial equilibrium with said gaseous material, said column means being exposed to an environment having a temperature lower than said water dew point temperature, said column means including a portion for transmitting a light signal through said liquid in said column means to detect turbidity in said liquid resulting from condensation of water in said material and between a light signal source means a light and signal receiver means of said apparatus;

first and second leg means each of which has a first end near said first end and said second end, respectively, of said column means and each of which is in fluid communication with said column means for circulating liquid through said column means, and third leg means being situated so that the second end of each of said first and second leg means opposite said first ends of said first and second leg means terminates in said third leg means to provide fluid communication between said first, second and third leg means and circulation of said liquid through said first leg means, said column means, said second leg means and said third leg means, said second leg means including inlet means to allow said gaseous material to be introduced into said apparatus, and said third leg means including outlet means to allow material to exit from said apparatus;

temperature indicator means for sensing the temperature of said liquid circulating through said column means; and means responsive to a change in the turbidity of said liquid in said column means as detected by said light signal receiver means to maintain said liquid circulating through said column means at a temperature at which the turbidity of said liquid increases and corresponds to the dew point temperature of water in said gaseous material.

2. The apparatus of claim 1 wherein said column means and said third leg means are substantially parallel, and said first leg means and said second leg means are substantially parallel.

3. The apparatus of claim 2 wherein said column means and said third leg means are substantially perpendicular to said first and second leg means.

4. The apparatus of claim 1 wherein said first, second and third leg means are structured and oriented so that at least a portion of said liquid in said column means passes into said first, second and third leg means prior to entering said column means.

5. The apparatus of claim 4 wherein:
   said outlet means includes a weir means situated so that substantially all material entering said first leg means is liquid, said outlet means comprises an outlet conduit adapted to be maintained at conditions so that substantially all material exiting said apparatus is vaporous, and a pressure regulator means is situated in association with said outlet conduit and acting to maintain a predetermined pressure in said apparatus.

6. The apparatus of claim 1 wherein:
   said signal receiver means includes a photoresistor located near said second end of said column means.

7. The apparatus of claim 1:
   wherein said means maintaining the temperature of said liquid comprises a heating means in contact with said column means and said first, second and third leg means to provide energy to control the temperature of said liquid in said column means and said leg means; and relay circuit means operable to energize said heating means.

8. The apparatus of claim 5 wherein said temperature indicator means includes a thermocouple situated in proximity to said first leg means to measure said temperature of said liquid.

9. The apparatus of claim 8 wherein said temperature indicator means further includes recording means capable of providing a record of said temperature of said liquid.

10. Apparatus for substantially continuously monitoring the water dew point temperature of a water, hydrocarbon-containing gaseous material flowing through a pipeline and wherein the water dew point temperature is lower than the hydrocarbon dew point temperature, said apparatus comprising:

column means forming a chamber operable to be filled with liquid formed from condensed portions of said gaseous material and in substantial equilibrium with said gaseous material, said column means being exposed to an environment having a temperature lower than said water dew point temperature, said column means including a portion for transmitting a light signal through liquid in said chamber to detect turbidity in said liquid resulting from condensation of water in said material and between a light signal source means and a light signal receiver means of said apparatus;

said column means including inlet means for conducting said water, hydrocarbon-containing gaseous material to said column means, and said column means being constructed in such a way that said gaseous material conducted to said column means through said inlet means provides for circulation of said liquid through said column means, and said column means includes outlet means operable to allow said gaseous material to exit from said apparatus;

temperature indicator means for sensing the temperature of said liquid circulating through said column means; and means responsive to a change in said turbidity of said liquid in said column means as detected by said light signal receiver means to maintain said liquid circulating through said column means at a temperature at which said turbidity of said liquid increases and corresponds to the dew point temperature of water in said gaseous material.

11. A method for substantially continuously determining the water dew point temperature of a water, hydrocarbon-containing gaseous material flowing through a pipeline and in which said water dew point temperature is lower than the dew point temperature of a hydrocarbon in said water, hydrocarbon-containing gaseous material, said method comprising:

(a) conducting at least a portion of said water, hydrocarbon-containing gaseous material through means forming a chamber exposed to a temperature sufficiently low enough to condense said hydrocarbon to form a liquid in said chamber, said temperature being less than said water dew point temperature, said liquid being in substantial equilibrium with said water, hydrocarbon-containing gaseous material at said temperature less than said water dew point temperature;

(b) measuring the intensity of a light signal conducted through at least a portion of said liquid to determine a change in turbidity of said liquid;

(c) controlling temperature of said liquid to maintain said liquid at a temperature corresponding substantially to said change in said turbidity of said liquid caused by condensation of water; and (d) measuring the temperature of said liquid at which said turbidity changes to determine the water dew point temperature of said water, hydrocarbon-containing gaseous material.

12. The method set forth in claim 11 wherein:

said chamber is formed in an elongated column having a first end and a second end, a first leg in flow communication with one end of said column, a second leg in flow communication with the other end of said column and a third leg interconnecting said first leg and said second leg to form a continuous flow path between said column and said first, second and third legs for said liquid.

13. The method of claim 12 wherein said water, hydrocarbon-containing gaseous material passes through an inlet in said second leg and the general direction of flow of said material passes said material sequentially through said second leg, said third leg, said first leg and said elongated column, provided that material in said first leg and said elongated column is substantially liquid.

14. The method of claim 13 wherein a portion of said water, hydrocarbon-containing gaseous material is removed from said third leg and does not flow through said first leg, and at least a portion of said liquid in said elongated column enters said second leg.

15. The method of claim 11 wherein step (e) comprises substantially continuously measuring said temperature and at least periodically recording said measured temperature.

16. The method of claim 11 wherein said water, hydrocarbon-containing gaseous material is natural gas or derived from natural gas.

* * * * *